United States Patent [19]

MacKeen

[11] Patent Number: 5,290,572
[45] Date of Patent: Mar. 1, 1994

[54] OPTHALMIC COMPOSITION FOR TREATING DRY EYE

[75] Inventor: Donald L. MacKeen, Bethesda, Md.

[73] Assignee: DEO Corporation, Bethesda, Md.

[21] Appl. No.: 926,244

[22] Filed: Aug. 6, 1992

[51] Int. Cl.$^5$ .................. A01N 59/26; A01N 59/06
[52] U.S. Cl. .................... 424/602; 424/686; 424/687; 424/696; 424/682; 514/574; 514/915
[58] Field of Search ............. 424/687, 686, 696, 682, 424/602; 514/574, 915

[56] References Cited

U.S. PATENT DOCUMENTS

| | | | |
|---|---|---|---|
| 3,843,778 | 10/1974 | Diamond et al. | 424/683 |
| 3,991,759 | 11/1976 | Urquhart | 424/427 |
| 4,131,651 | 12/1978 | Shah et al. | 424/78.04 |
| 4,327,076 | 4/1982 | Puglia et al. | 424/686 |
| 4,370,325 | 1/1983 | Packman | 514/335 |
| 4,407,791 | 10/1983 | Stark | 424/78.04 |
| 4,409,205 | 10/1983 | Shively | 424/78.04 |
| 4,744,980 | 5/1988 | Holly | 424/78.04 |
| 4,775,531 | 10/1988 | Gilbard | 424/606 |
| 4,818,537 | 4/1989 | Guo | 424/427 |
| 4,883,658 | 11/1989 | Holly | 514/772.3 |
| 4,914,088 | 4/1990 | Glonek et al. | 514/76 |
| 4,957,918 | 9/1990 | Martin et al. | 514/235.8 |
| 4,961,683 | 8/1990 | Davis | 128/734 |
| 4,966,773 | 10/1990 | Gressel et al. | 424/489 |
| 5,041,434 | 8/1991 | Lubkin | 514/914 |
| 5,075,104 | 12/1991 | Gressel et al. | 514/915 |

OTHER PUBLICATIONS

Dohlman. 1971. Trans. Ophthal. Soc. U. K. 91:105.
Huth et al. 1981. Arch. Ophthal. 99:1628.
Lamberts. 1980. International Ophthamology Clinics. 20:63.
Lemp. 1973. International Ophthamology Clinics. 13:145.
MacKeen. 1980. International Ophthamology Clinics. 20:79.
Pavan-Langston. 1973. International Ophthalmology Clinics. 13:231.
Wright. 1971. Trans. Ophthal. Soc. U. K. 91:119.
Flynn. 1986. The Preocular Tear Film, Lamberts & MacKeen, eds, pp. 212-220.
Götz et al. 1986. The Preocular Tear Film, Lamberts & MacKeen, eds, pp. 230-238.
Foulks. 1986. The Preocular Tear Film, Lamberts & MacKeen, eds, pp. 271-279.
Tseng. 1986. The Preocular Tear Film, Lamberts & MacKeen, eds, pp. 253-270.

*Primary Examiner*—Allen J. Robinson
*Assistant Examiner*—John D. Pak
*Attorney, Agent, or Firm*—Raymond B. Cranfill

[57] ABSTRACT

An ophthalmologic composition therapeutic in the treatment of dry eye syndrome is disclosed. The composition is comprised of a minimally soluble salt of calcium that has been finely divided into particles having a mean diameter of 10 to 60 microns. The calcium salt particles are suspended within a pharmacologically acceptable carrier such as petrolatum or physiological saline. The composition is delivered to the ocular surface in an amount and for a time sufficient to alleviate the symptoms of dry eye.

7 Claims, No Drawings

OPTHALMIC COMPOSITION FOR TREATING DRY EYE

FIELD OF THE INVENTION

This invention relates generally to the treatment of dry eye syndrome and more particularly to providing topical compositions capable of relieving the symptoms of dry eye syndrome.

REFERENCES

Dohlman. 1971. Trans. Ophthal. Soc. U.K. 91:105.
Huth et al. 1981. Arch. Ophthal. 99:1628.
Lamberts. 1980. International Ophthalmology Clinics 20 (3):63.
Lemp. 1972. International Ophthalmology Clinics. 12.221.
Lemp. 1973. International Ophthalmology Clinics. 13.145.
MacKeen. 1980. International Ophthalmology Clinics 20 (3):79.
Pavan-Langston. 1973. International Ophthalmology Clinics. 13:231.

BACKGROUND OF THE INVENTION

Dry eye, also known as keratoconjunctivitis sicca, is a common ophthalmological disorder affecting millions of Americans each year. The condition is particularly widespread among post-menopausal women due to hormonal changes following the cessation of fertility.

Dry eye may afflict an individual in varying severity. In mild cases, a patient may experience burning, a feeling of dryness, and persistent irritation such as is often caused by small bodies lodging between the eye lid and the eye surface. In severe cases, vision may be substantially impaired. Good reviews of the dry eye syndrome and standard methods of treatment may be found in Dohlman (1971) and Lemp (1973).

Although it appears that dry eye may result from a number of unrelated pathogenic cause, all presentations of the syndrome share a common effect, that is the breakdown of the pre-ocular tear film, which results in dehydration of the exposed outer surface and many of symptoms outlined above.

Practitioners have taken several approaches to the treatment of dry eye. One common approach has been to supplement and stabilize the preocular tear film using so-called artificial tears. Another approach has been the use of ocular inserts that function variously to provide a tear substitute or to stimulate endogenous tear product.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids. Examples of these treatment approaches are disclosed in U.S. Pat. Nos. 4,131,651 to Shah et al.; 4,370,325 to Packman; 4,409,205 to Shively; 4,744,980 and 4,883,658, both to Holly; 4,914,088 to Glonek; and 5,057,104 to Gressel et al.

United States Patents directed to the use of ocular inserts in the treatment of dry eye include U.S. Pat. No. 3,991,759 to Urquhart. The use of ocular inserts is also discussed in detail in Lamberts (1980).

Another recent approach involves the provision of lubricating substances in lieu of artificial tears. U.S. Pat. No. 4,818,537 to Guo discloses the use of a lubricating, liposome-based composition. U.S. Pat. No. 4,966,773 discloses the use of microfine particles of one or more retinoids.

Aside from the above efforts, which are directed primarily to the alleviation of symptoms associated with dry eye, also known are methods and compositions directed to treatment of the dry eye condition. For example, U.S. Pat. No. 5,041,434 discloses the use of sex steroids, such as conjugated estrogens, to treat dry eye condition in post-menopausal women.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

The use of ocular inserts is also problematic. Aside from cost, they are often unwieldy and uncomfortable. Further, as foreign bodies, they run a risk of infection to the eye. In situations where the insert does not itself produce and deliver a tear film, artificial tears must still be delivered on a regular and frequent basis. Indeed, Pavan-Langston (1973) has concluded that, as a rule, ocular inserts are not very effective in the treatment of many dry eye conditions.

In view of the foregoing, there is a clear need for an effective treatment for dry eye that is capable of alleviating symptoms, as well as treating the underlying physical and physiological deficiencies of the syndrome, and that is both convenient and inexpensive to administer.

SUMMARY OF THE INVENTION

It is an object of the invention to provide a composition for the treatment of dry eye syndrome.

It is another object of the invention to provide a composition for the treatment of dry that is easy and convenient to administer.

Yet another object of the invention is to provide a composition for the treatment of dry eye that does not require continual or even frequent delivery to the eye in order to be effective.

A further object of the invention is to provide a composition for the treatment of dry eye that is inexpensive.

Still another object of the present invention is to provide a method for utilizing the composition of the invention in the treatment of dry eye syndrome.

The invention meets these objects by providing a minimally water-soluble, calcium-based composition that is delivered directly or indirectly to the ocular surface. Calcium in this composition is present as a more or less water insoluble salt, such as calcium carbonate. The calcium salt is finely divided into particles having mean diameters of between 15 to 60 microns. This can be achieved by conventional methods of more simply by levigating the salt with either glycerol or propylene glycol. The finely divided calcium salt is then dispersed in a pharmacologically acceptable carrier. The carrier may be either hydrophobic or hydrophilic in nature. In a preferred embodiment, the finely divided salt is dispersed in a hydrophobic carrier such as petrolatum.

Unlike previous workers in this area, it has been discovered that calcium plays a key role in the development and maintenance of the preocular tear film and that the delivery of calcium in a slowly solubilized, ionic form to the exposed ocular surfaces not only alleviates symptoms of discomfort and the feeling of dryness as well as symptoms such a conjunctival and lid margin redness, but may help correct underlying physical and physiological deficiencies responsible for the dry eye condition.

The composition of the present invention is not only therapeutically effective, but also is cost effective and easy to administer. Unlike existing artificial tear or drug therapies, calcium carbonate and the carriers disclosed below, such as petrolatum and saline solution, are inexpensive. Further, the low solubility of calcium carbonate under physiological conditions in the eye ensures that a single application of the composition will release sufficient calcium ion into the tear film over much of the patient's waking hours, thereby obviating the need for frequent and liberal application that is the rule with known tear substitutes.

These and other objects and advantages of the invention will become more fully apparent after reading the following detailed description of the invention and examples.

DETAILED DESCRIPTION OF THE INVENTION

The present invention comprises a minimally water-soluble, calcium-based composition that may be administered directly to the ocular surfaces or may be administered through the use of ocular inserts or by placing the composition on the skin of the lateral or inferior lid margins.

The composition itself is derived from a physical mixture of a poorly water-soluble calcium salt and a pharmacologically acceptable carrier. It is important that the calcium salt be very finely divided, preferably into microfine particles having a mean diameter of 60 microns or less. In one embodiment in which the composition carrier is hydrophobic, the mean particle diameter is 10 to 60 microns. In another embodiment in which the composition carrier is hydrophilic, the mean particle diameter is 10 microns or less. Division of the calcium salt into microfine particles may be accomplished by any standard means, such as pulverization in a mortar and pestle, or more simply by levigation with the polyol such as glycerol or propylene glycol.

It is also important that the calcium salt selected be largely insoluble in water. This will ensure a slow release over time of calcium ion into the tear film, thereby obviating the need for continuous or frequent application of the composition. Suitable calcium salts include calcium carbonate (CaCo), calcium tartrate ($CaC_4H_4O_6$), calcium magnesium carbonate ($CaCO_3 MgCO_3$), calcium metasilicate ($CaSiO_3$), calcium sulfate ($CaSO_4$), calcium malate ($Ca_4H_4O_5$), secondary calcium orthophosphate ($CaHPO_4$), and similar poorly water soluble calcium salts that are physiologically compatible and stable. Among these calcium carbonate, with a solubility of 0.0014 gm/100 ml in cold water, is preferred.

Turning now to the carrier, either hydrophobic or hydrophilic carriers are acceptable, although a hydrophobic carrier is preferred because it tends to be washed from the eye much less quickly than a typical hydrophilic carrier and can be applied to the external to the eye. A suitable, pharmacologically acceptable, hydrophobic carrier is petrolatum. The melting point of petrolatum may be increased by the admixture of a suitable substance such as white wax. Suitable, pharmacologically acceptable, hydrophilic carriers include physiological saline, with or without viscosity enhancing agents to delay wash-out, such a methyl cellulose, hydroxyethyl cellulose, hydroxypropylmethyl cellulose, carboxymethyl cellulose, polyethyleneoxide, and dextrans, along with any of the artificial tear formulations disclosed in the following U.S. patents, the contents of which are herein incorporated by reference: U.S. Pat. No. 4,131,651, to Shah, et al.; U.S. Pat. No. 4,409,205 to Shively; U.S. Pat. Nos. 4,744,980 and 4,883,658, both to Holly; U.S. Pat. No. 5,075,104 to Gressel et al.

It will be apparent that the use of calcium ion to treat dry eye does not necessarily exclude the use of other known therapies. It should be possible to combine the delivery of calcium with that of other known therapies, such as the use of retinoids, estrogens, and the like. However, one must be careful to avoid compositions that include chelating or other binding agents having an affinity for ionic calcium.

The composition of the invention may be applied topically to the eye, either directly, indirectly or through the use of an ocular insert. Direct application to the eye surface is best accomplished by instilling a preparation of the composition that has a hydrophilic carrier, such as drops of a saline or artificial tear solution containing a calcium salt.

Indirect application may be accompanied by placing a small quantity of the composition on the skin of the lateral or inferior lid margins. This enables the entrance of small volumes of the composition into contact with the fluid in the tear meniscus, and presumably thence into the preocular tear film. Although not wishing to be bound by any theory of operation, it is hypothesized that movement of the composition into the liquid between the interphalpebral space occurs through the interaction of several mechanisms. First, the petrolatum-based vehicle melts at body temperature without evaporating, resulting in a flow over the lid margin. Transport into the tear meniscus, and ultimately into the tear film, is probably accomplished by movement of the orbicularis orbis muscle of the lid, which causes lateral movement of the lower lid during the blink. Although the results of such passage have been shown by the relief of symptoms and signs, evidence of such action has also been gained by the application of the composition containing 6% sodium fluorescein in petrolatum. This soluble salt could be visualized four minutes after application and could be seen up to 40 minutes later. No fluorescence was observed during this interval following the placement of an identical ointment containing fluorescein acid.

Finally, for indirect delivery an ocular insert, especially one designed to be physiologically compatible with placement in the inferior cul de sac of the eye can be impregnated with the calcium salt. Upon insertion it would act to release the calcium ion directly to the eye's surfaces.

The optimal active component is one that is miscible with the hydrophobic vehicle yet is water soluble. More effective action may be obtained from components that are potentially water soluble.

EXAMPLES

EXAMPLE I

Preparation of Hydrophobic Composition

The calcium salt is finely divided by any standard means, such as pulverization in a mortar and pestle, or more simply by levigation with a polyol such as glycerol or propylene glycol. The finely divided powder or the polyol mixture is then admixed with a neutral ointment base such as petrolatum. In order to delay release of the calcium ion, substances with a higher melting point, such as white wax, may be admixed with the petrolatum to prolong passage of the preparation. A suitable hydrophobic preparation includes 2% to 25% weight by volume of the desired calcium salt.

EXAMPLE II

Preparation of Hydrochilic Composition

The desired calcium salt is first pulverized as described in Example I. Either the finely divided calcium salt or the polyol mixture is then admixed with an appropriate aqueous solution such as normal saline or a mixture of sodium and potassium chlorides to mimic the ratio in normal tear fluid. The viscosity may be increased to suitable physiological levels by the addition of suitable viscosity increasing agents such as methyl cellulose, hydroxyethyl cellulose, hydroxypropylmethyl cellulose, carboxymethyl cellulose, ployethyleneoxide, and dextrans, along with any of the artificial tear formulations disclosed in the foregoing specification. A suitable hydrophobic preparation includes 0.05% to 5% weight by volume of the desired calcium salt.

EXAMPLE III

Treatment Protocol

Hydrophobic preparation

Frequency of use: once or twice daily, and following face washing.

Length of benefit: 3 hours or longer.

Degree of therapeutic benefit: significant alleviation of dry eye symptoms, including irritation, scratchiness and excessive tearing.

Hydrophilic preparation

Frequency of use: 3-4 times daily.

Length of benefit: 2 hours or longer.

Degree of therapeutic benefit: significant alleviation of dry eye symptoms, including irritation, scratchiness and excessive tearing.

EXAMPLE IV

Clinical Findings, Group I

A first group comprised three persons, two female and one male, ranging in ages from 60 to 70 years. No member of the group was a contact lens wearer. The females had keratoconjunctivitis sicca ("KCS") in varying severity, the male had chronic seborrheic tear film instability. Conventional treatment with tear substitutes provided transient relief at best.

To date, all have been successfully treated with daily application of the hydrophobic formulation of Example I for more than four months. There have been no detectable side effects.

Female I had long-standing KCS. She was treated by a single daily application of the hydrophobic formulation of Example I having a 10% weight by volume content of calcium carbonate. The formulation was applied to the skin immediately adjacent to each lateral canthus. Noticeable relief of symptoms occurred within 20 to 30 minutes later. Daily application was followed by complete disappearance of burning, itching, redness and epiphora. Reapplication was necessary on a daily basis and after face washing.

Female II had milder KCS than female I, exhibiting no epiphora. She was treated identically as female I. Signs and symptoms of KCS improved markedly following application of the formulation. Reapplication was necessary on a daily basis and after face washing.

Male I suffered from chronic seborrheic film instability. Male I was treated identically to Female I. After application, visual acuity improved from 20/40 to 20/20 or 20/15. Relief of symptoms was enhanced when the formulation was applied to margin of lower lid morning and at bedtime. Reapplication was necessary on a daily basis and after face washing.

EXAMPLE V

Clinical Findings, Group II

A second patient population comprising 30 individuals ranging in ages from 45 to 88 years was studied. Two members of the group were diabetic, 1 was leukemic. All patients were selected on the basis of being chronic, poorly responsive to conventional treatments and exhibiting clinically obvious signs of tear problems such as bulbar injection and lid redness. Purely objective assessment of improvement was therefore possible from serial photographic records. Patients with tear meniscal widths less than 0.1 mm were excluded.

Each patient was treated with the hydrophobic composition of Example I containing 10% weight by volume of calcium carbonate. The composition was applied daily by the clinic ophthalmologist. Most patients were treated once daily at 8:00 am. The severest cases were treated three times a day. The longest course of treatment lasted 8 weeks. All but three patients showed objective and subjective improvement; of these, one did not return and two were discontinued after one week because of lack of objective improvement. Some patients required only once or twice weekly treatment. There were no allergic responses; no condition worsened.

EXAMPLE VI

Effect of Other Divalent Cations

The effect of magnesium, the other main divalent cation in normal tears, on dry eye was studied. A hydrophobic composition according to Example I, containing 10% weight by volume of magnesium carbonate, was tested for its effect on symptoms and signs of dry eye. The composition was administered to each of the patients described in Example VI. No detectable improvement in either signs or symptoms was detected. The same results were obtained in a masked study on these same individuals.

From the foregoing, it can now be appreciated how the objects and features of the invention are met. The composition of the invention provides a ready source of calcium ion when applied to the ocular surface. Because the ionic calcium is derived from a calcium salt that is minimally soluble in water, slow, long term release of ionic calcium into the tear film is assured.

The invention is clearly advantageous over known treatments in that long term relief of symptoms can be achieved with a minimum number of applications, generally once daily. Presently available dry eye treatments have durations of effectiveness that can be measured in mere minutes. According to Lemp (1972), the actual retention time of instilled artificial tears is in the order of minutes, a period inadequate to provide comfort for the severe dry eye patient. This situation has not significantly changed in the ensuing years.

The present invention is further advantageous in that it is directed to both the treatment of the underlying cause of dry eye as well as the relief of symptoms resulting from a dry eye condition.

The invention is also advantageous in its ease of administration. The administration of conventional dry eye preparations poses a problem especially for the older presbyopic patient. Proper placement of either drops or ointment without self-inflicted ocular injury can be difficult even to the normal sighted, requiring positional gymnastics and a steady hand. In contrast, use of the hydrophobic-based composition of the present invention permits application to the lid margins, a move that can be simply accomplished without undue risk of eye injury.

Although the invention has been described with respect to a particular calcium-bearing composition and method of use in treating dry eye syndrome, it will be appreciated that various modifications of the composition and method are possible without departing from the invention, which is defined by the claims set forth below.

I claim:

1. A method for treating a patient afflicted with dry eye comprising the steps of:
    a) providing a calcium-based ophthalmic composition comprising a finely divided, minimally water-soluble, ophthalmologically acceptable calcium salt suspended in an ophthalmologically acceptable carrier; and
    b) applying said calcium-based ophthalmic composition adjacent to lateral or inferior lid margins exterior to an ocular surface in a sufficient amount and for sufficient time to alleviate dry eye, wherein blinking action of the lid margins cuts off and carries into the eye small amounts of the composition thereby effecting treatment of the dry eye condition.

2. The method of treating a patient afflicted with dry eye of claim 1 wherein said ophthalmologically acceptable carrier is hydrophobic.

3. The method of treating a patient afflicted with dry eye of claim 2 wherein said ophthalmologically acceptable carrier is petrolatum.

4. The method of treating a patient afflicted with dry eye of claim 1 wherein said ophthalmologically acceptable calcium salt is selected from the group consisting of calcium carbonate, calcium tartrate, calcium magnesium carbonate, calcium metasilicate, calcium sulfate, calcium malate, secondary calcium orthophosphate.

5. A method of treating a patient afflicted with dry eye comprising the step of:
    a) providing a calcium-based ophthalmic composition consisting essentially of a finely divided, ophthalmologically acceptable grade of calcium carbonate suspended in a ophthalmologically acceptable grade of petrolatum; and
    b) applying said calcium-based ophthalmic composition adjacent to lateral or inferior lid margins exterior to an ocular surface in a sufficient amount and for sufficient time to alleviate dry eye.

6. The method for treating a patient afflicted with dry eye comprising the steps of:
    a) providing a calcium-based ophthalmic composition comprising a finely divided, minimally water-soluble, ophthalmologically acceptable calcium salt suspended in a ophthalmologically acceptable hydrophobic carrier, wherein said calcium salt is divided into particles having a mean diameter of 10 to 60 microns; and
    b) applying said calcium-based ophthalmic composition adjacent to lateral or inferior lid margins exterior to an ocular surface in a sufficient amount and for sufficient time to alleviate dry eye, wherein blinking action of the lid margins cuts off and carries into the eye small amounts of the composition thereby effecting treatment of the dry eye condition.

7. A method for treating a patient afflicted with dry eye comprising the steps of:
    a) providing a calcium-based ophthalmic composition comprising a finely divided, minimally water-soluble, ophthalmologically acceptable calcium salt suspended in petrolatum, wherein said calcium salt is divided into particles having a mean diameter of 10 to 60 microns; and
    b) applying said calcium-based ophthalmic composition adjacent to lateral or inferior lid margins exterior to an ocular surface in a sufficient amount and for sufficient time to alleviate dry eye, wherein blinking action of the lid margins cuts off and carries into the eye small amounts of the composition thereby effecting treatment of the dry eye condition.

* * * * *

UNITED STATES PATENT AND TRADEMARK OFFICE
CERTIFICATE OF CORRECTION

PATENT NO. : 5,290,572

DATED : March 1, 1994

INVENTOR(S) : Donald L. Mackeen

It is certified that error appears in the above-indentified patent and that said Letters Patent is hereby corrected as shown below:

In the title page, ITEM: 54, the word "OPTHALMIC" should read -- OPHTHALMIC -- : ITEM: 56, OTHER PUBLICATIONS, insert the word -- Holly, -- after the words "Tear Film," and before the word "Lamberts", in lines 11, 13, 15, and 17 of the second column.

In column 1, line 1, the word "OPTHALMIC" should read -- OPHTHALMIC --.

In column 2, line 39, insert the word -- eye -- after the word "dry" and before the word "that" : line 57, the number "15" should read -- 10 -- : line 58, the word "of" should read --or--

UNITED STATES PATENT AND TRADEMARK OFFICE
CERTIFICATE OF CORRECTION

PATENT NO. : 5,290,572

DATED : March 1, 1994

INVENTOR(S) : Donald L. Mackeen

It is certified that error appears in the above-indentified patent and that said Letters Patent is hereby corrected as shown below:

In column 3, line 64, cancel the words "to the", between the word "applied" and the word "external".

In column 4, line 35, the word "interphalpebral" should read -- interpalpebral --.

In column 5, line 12, "Hydrochilic" should read -- Hydrophilic -- : line 26, the word "hydrophobic" should read -- hydrophilic --.

Signed and Sealed this

Eighth Day of November, 1994

Attest:

BRUCE LEHMAN

*Attesting Officer*       *Commissioner of Patents and Trademarks*